United States Patent [19]

Jermyn

[11] Patent Number: 4,479,672
[45] Date of Patent: Oct. 30, 1984

[54] CONTACT LENS INSERTER

[76] Inventor: Arthur C. Jermyn, 15914 Overview Rd., Poway, Calif. 92064

[21] Appl. No.: 436,504

[22] Filed: Jan. 5, 1983

[51] Int. Cl.$^3$ .............................................. A61F 9/00
[52] U.S. Cl. ................................................. 294/1 CA
[58] Field of Search .................... 294/1 CA, 25, 64 R; 128/303 R; 206/5.1

[56] References Cited

U.S. PATENT DOCUMENTS

| | | | |
|---|---|---|---|
| 3,645,576 | 2/1972 | Horres | 294/1 CA |
| 3,743,337 | 7/1973 | Crary | 294/1 CA |
| 3,879,076 | 4/1975 | Barnett | 294/1 CA |
| 4,126,345 | 11/1978 | List | 294/1 CA |
| 4,167,283 | 9/1979 | Feldman | 294/1 CA |
| 4,200,320 | 4/1980 | Durham | 294/1 CA |

Primary Examiner—Johnny D. Cherry
Attorney, Agent, or Firm—Lloyd F. Seebach

[57] ABSTRACT

The invention relates to a contact lens inserter which retains and holds a contact lens thereon by means of a viscous fluid that is placed in a cup-shaped part forming a portion of the inserter. The inserter per se comprises the cup-shaped portion and a handle integral therewith, the handle consisting of a first and a second portions which are angularly disposed relative to each other and to the planar surface of the cup-shaped portion, the latter being integral with the free end of the second portion. The angular relationship of the portions of the inserter is such that the fingers of the user that are manipulating the inserter are displaced from the user's eyes to such an extent that no sight or image interference is apparent to the user.

3 Claims, 5 Drawing Figures

CONTACT LENS INSERTER

FIELD OF THE INVENTION

The invention relates to contact lenses and more particularly to a contact lens inserter for viscously holding a contact lens as the latter is placed or positioned in intimate contact with the eye of a contact lens user.

DESCRIPTION OF THE ART

It is common practice to apply a contact lens, particularly of the "soft type," to the cornea of an eye with a wetted index finger. This practice is difficult to accomplish with any ease, accuracy or safety. Depending on the position of the lens on the wetted finger, the finger nail, if rather long, could present a real danger in that the cornea could be scratched by the nail. In the event a mirror is used, the wetted finger on which the lens is placed is usually of such breadth that it could block most, if not all, of the mirror image of the eye so the mirror, in effect, is useless when it is really needed most, that is, when the lens is in very close proximity to the eye.

Applicators of various types are available for applying a contact lens to the eye of a user. In most instances, the contact lens is usually gripped about its peripheral edge or flange in such a manner that the user can peer or look through the lens as it is brought into position with respect to the eye. With such applicators, release of the lens when it is very close to the eye presents a problem. In some cases this problem is circumvented by placing the contact lens on or within a ring, but this does not alleviate the problem because the lens cannot be easily released from the applicator.

SUMMARY OF THE INVENTION

It is an object of the invention to provide a contact lens inserter which viscously holds the lens on the inserter as the inserter is moved toward the eye to position the lens on the eye with a minimum of effort and with ease of release of the lens from the inserter.

Another object of the invention is to provide a contact lens inserter having a hemispherical or cup-shaped portion for receiving a viscous fluid which holds the lens on the cup-shaped portion, the cup-shaped portion being angularly disposed relative to the inserter handle with which it is integral so as to keep the user's finger engaging the handle away from the eyes, particularly at the time the inserter is close to the eye to position the lens on the eye.

Still another object of the invention is to provide a contact lens inserter having a hemispherical or cup-shaped portion for receiving a viscous fluid, the cup-shaped portion being provided with a recess at the bottom thereof for increasing the fluid volume and the viscous holding force on a contact lens in engagement therewith.

Yet another object of the invention is to provide a contact lens inserter comprising a handle having a first portion engageable by the fingers of a user for manipulating the inserter and a second portion extending from one end of the first portion and inclined at an angle thereto, and a hemispherical or cup-shaped portion for receiving a viscous fluid which contacts the spherical surface of the lens to hold the latter on the inserter, the planar surface of the cup-shaped portion being angularly disposed relative to the first portion of the handle and at an angle to the second portion of the handle that is smaller than that of the first portion,, thereby permitting the lens to be brought into contact with the eye with no interference from the fingers holding the inserter.

And still another object of the invention is to provide a contact lens inserter that is simple in structure and operation and alleviates the problems associated with the insertion of a contact lens relative to the eye.

These and other objects and advantages of the invention will be apparent to those skilled in the art by the description which follows and which is made in conjunction with the accompanying drawing.

Briefly, the objects of the invention are attained by utilizing a single member comprising three distinct but integrally associated parts. The handle includes a first portion and a second portion, these portions being integral and coextensive as well as arranged at an angle relative to each other. The free end of the second portion carries a hemispherical or cup-shaped portion that is hollow and is provided with a recess in the bottom thereof. The planar surface of the hemispherical portion is arranged at an angle to both the first and second portions of the handle and at a greater angle to the first portion than to the second portion. In use, the first portion of the handle is engaged by at least two fingers of the user, either the right or left hand, and held in a position so the planar surface of the hemispherical portion is level. A viscous fluid is then placed in the cup-shaped portion and the lens is then placed thereon with the spherical surface of the lens extending into the cup-shaped portion and in contact with the fluid. The recess in the bottom of the cup-shaped portion permits an additional amount of fluid to be placed in the cup-shaped portion, thereby increasing the viscous holding force or capillary attraction between the curved surface of the lens and the fluid. The inserter with the lens thereon is moved toward the eye as the head is maintained in a lowered position. The angular relationship of the respective portions of the inserter is such that the fingers holding and manipulating the inserter cannot come in close proximity to the eye and, hence, the tendency of the user to close the eyes as the lens is moved closer to the eye is alleviated. When the lens is in contact with the eye and properly positioned thereon, the lids are closed and the inserter is tilted slightly to break the holding force of the fluid and then gently removed, the lens being held and maintained in position on the eye by the lids until the inserter has been fully recovered.

DESCRIPTION OF THE DRAWINGS

Reference is now made to the accompanying drawings wherein like reference numerals designate like parts and wherein.

DESCRIPTION OF A PREFERRED EMBODIMENT

Figure 1:
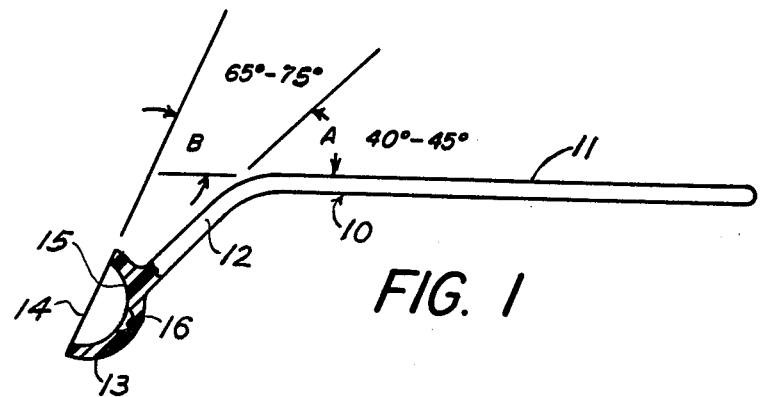
FIG. 1 is a side elevational view, partially in section, of a contact lens inserter in accordance with the invention.

With reference to the drawings and particularly FIG. 1, a contact lens inserter in accordance with the invention is generally designated by the numeral 18. The inserter 10 comprises essentially three integral portions, namely, a first portion or finger-engaging part 11, a second portion or intermediate part 12, portions 11 and 12 constituting, in effect, a handle, and a third portion 13 that is hemispherical or cup-shaped, as shown more clearly in FIG. 4.

Figure 2:
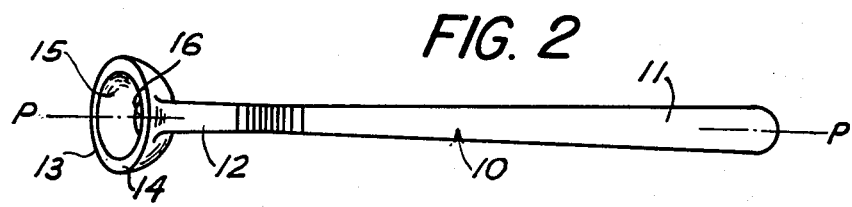
FIG. 2 is a top plan view of the contact lens inserter shown in FIG. 1.
Figure 3:
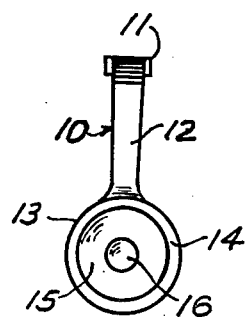
FIG. 3 is a left end elevational view of the contact lens inserter shown in FIG. 1.

As shown in FIG. 2, the inserter 10 is generally symmetrical about a central plane P—P. However, with respect to FIG. 1, it will be noted that the second portion 12 is inclined at an angle A to the first portion 11, the angle A being about 40-45 degrees. Also, the planar surface 14 of the portion 13 is inclined at an angle of about 60-75 degrees to the first portion 11 for a reason to be explained hereinafter. The portion 13 is hollowed out, as shown by the numeral 15, to form a cup-shaped depression at the bottom of which there is provided a recess or depression 16.

The contact lens inserter 10 is molded of a plastic material that is impervious to the eye or eye liquid, such as tears. With portions 11, 12 and 13 off-set with respect to one another at the angles A and B, the fingers of the user that grip the portion 11 are quite far removed from the eyes, irrespective of the eye on which the contact lens is to be placed. Also, the angular relationship of portions 11, 12 and 13 permit the inserter 10 to bridge the user's nose 20 regardless of which hand is used to grasp the inserter. This is shown graphically in FIG. 5 where the inserter 10 is assumed to be grasped by the fingers of the left hand. Such displacement of the portions 11, 12 and 13 tends to eliminate the fear a person may have as to any object that is moved toward the eye.

Figure 4:
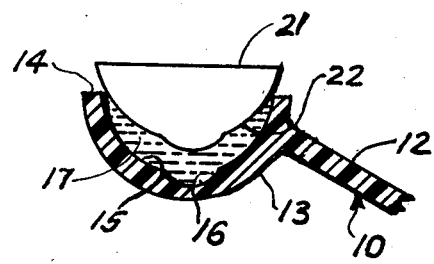
FIG. 4 is an enlarged sectional view of the hemispherical or cup-shaped portion of the contact lens inserter shown in FIG. 1 and showing the position normally assumed by the contact lens on the inserter after a viscous fluid has been added or placed in the cup-shaped portion.

In use, the portion 11 is grasped by several fingers of the hand of the user that is most easily manipulative for the task. The inserter 10 is then held in such a position that the planar surface 14 of the portion 13 is level, as seen in FIG. 4. Several drops of a liquid 17, such as a water soluble polymer, is then placed in the depression 15. As is well known, the corneal surface of the eye is hydrophobic and natural tears contain mucin. Dextrans are used in opthalmic solutions and when modified by a proper thickener, such as ethycellulose or benzalkonium chloride, can be used in the present application. A saline solution can also be used but it would not have or provide the holding force of the above-mentioned Dextran solutions. However, any solution that might be used must have a natural ph value that is compatible with the natural tear solution of the eye.

After the solution has been placed in the depression 15, the contact lens 21 is then positioned on the portion 13 with the curved surface 22 thereof extending into the depression 15. The viscosity of the liquid 17 determines the holding force or capillary attraction exerted on the lens 21 to maintain it in position on the planar surface 14 and on the inserter 10. The provision or addition of the recess 16 permits an additional amount of liquid to be added to the portion 13. It has been found that this additional liquid, although small in amount, does add to the holding force or capillary attraction.

Figure 5:
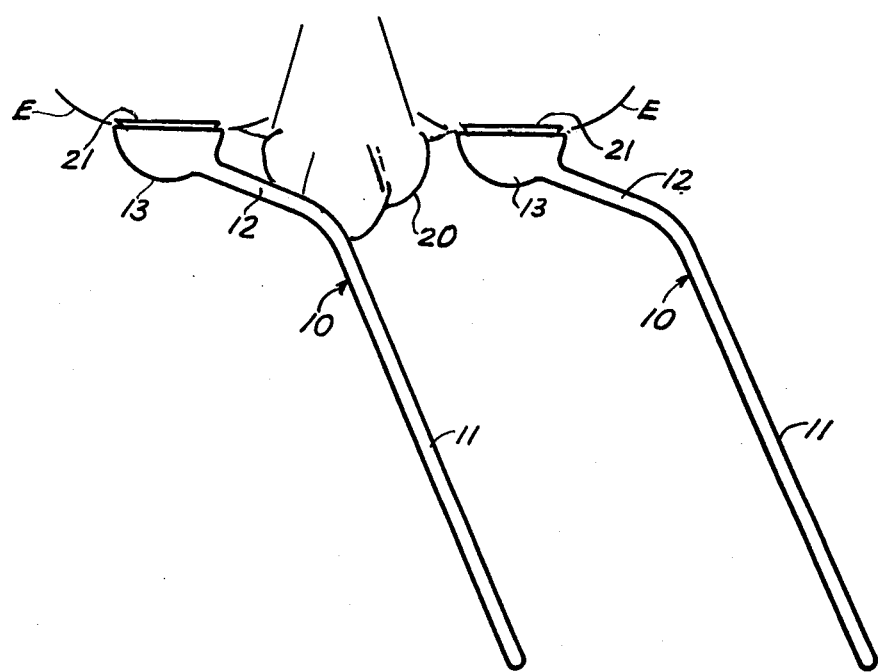
FIG. 5 is a diagrammatic view showing the relation of first or finger-engaging portion of the inserter to either eye of the user when the inserter is held in the left hand, a mirror image effect being accomplished when the inserter is held in the right hand.

With the lens 21 positioned on the planar surface 14, the inserter 10 is held so as to maintain the surface 14 as level as possible as the lens is moved toward the eye E. At the same time, the head is moved forward toward and over the inserter 10. The inserter 10 with the lens 21 thereon is then in the position shown in FIG. 5. It will be evident that the angular relationship of the portions 11, 12 and 13 is such that the fingers grasping the portion 11 do not and cannot be brought in close proximity to the eye E even when the lens 21 is actually in contact with the eye. Once the contact lens 21 is positioned on the eye E and properly oriented as to the cornea, the eyelids are partially closed to engage at least part of the lens and the portion 13. Then with a very slight twisting action imparted to the inserter 10 by the fingers grasping the portion 11, the holding force or capillary attraction between the lens 21 and the liquid 17 is broken, thereby permitting withdrawal of the inserter 10. Again, it should be pointed out that reaching over the nose with the inserter 10, whether from the left or right side, still maintains the fingers out of close proximity to the eye on which the lens is being placed as well as to the other eye, as shown in FIG. 5.

From the above description, it has been shown that the contact lens inserter 10 in accordance with the invention is truly simple in construction and meets a dire need. While no mention has been made hereinbefore of the size of such contact lens inserter, it is to be understood that the size of the portion 13 is the controlling factor because "soft" contact lenses are much smaller than "hard" contact lenses. The contact lens inserter for the "soft" type of lens would require that portion 13 be about 5/16 of an inch in diameter. The same angular relationship of the portions 11, 12 and 13 can be used for a "hard" contact lens inserter but the size of portion 13 would have to be increased considerably to conform to the lens size.

This invention has been described in detail with particular reference to preferred embodiments thereof, but it will be understood that variations and modifications may be effected within the spirit and scope of the invention.

I claim:

1. A contact lens inserter consisting of a single member for viscously holding a contact lens on one end thereof and for placing the contact lens in intimate contact with the eye of a contact lens user, comprising:
   a handle having a first generally flat portion engageable by at least two fingers of the user for manipulating the inserter and a second generally flat portion coextensive with and extending from one end of the first portion at an acute angle thereto; and
   a contact lens holding means integral with the free end of the second portion, the holding means being generally hemi-spherical in shape, having a planar surface angularly displaced relative to the second portion at a second acute angle that is smaller than the first-mentioned acute angle, and hollowed to provide a recess for receiving a viscous fluid to hold the contact lens placed on the planar surface with the curved surface thereof extending into the recess and into contact with the fluid.

2. A contact lens inserter in accordance with claim 1 wherein the recess is provided in the bottom thereof with a well to increase the fluid volume, thereby increasing the viscous holding force.

3. A contact lens inserter in accordance with claim 1 wherein the second portion is inclined at an angle of 40-45 degrees relative to the first portion and the planar surface is inclined at an angle of 65-75 degrees relative to the first portion.

* * * * *